United States Patent [19]
Brisken

[11] Patent Number: 5,728,062
[45] Date of Patent: Mar. 17, 1998

[54] APPARATUS AND METHODS FOR VIBRATORY INTRALUMINAL THERAPY EMPLOYING MAGNETOSTRICTIVE TRANSDUCERS

[75] Inventor: Axel F. Brisken, Fremont, Calif.

[73] Assignee: Pharmasonics, Inc., Mountain View, Calif.

[21] Appl. No.: 566,740

[22] Filed: Nov. 30, 1995

[51] Int. Cl.$^6$ .................................................. A61B 17/20
[52] U.S. Cl. ............................................. 604/22; 606/169
[58] Field of Search ..................... 606/169; 607/97; 604/22; 601/2; 310/26

[56] References Cited

U.S. PATENT DOCUMENTS

| | | | |
|---|---|---|---|
| 3,433,226 | 3/1969 | Boyd | 128/305 |
| 3,565,062 | 2/1971 | Kuris | 128/24 |
| 4,184,092 | 1/1980 | Wieser | 310/316 |
| 4,636,195 | 1/1987 | Wolinsky | 604/53 |
| 4,692,139 | 9/1987 | Stiles | 604/22 |
| 4,698,058 | 10/1987 | Greenfeld et al. | 604/266 |
| 4,808,153 | 2/1989 | Parisi | 604/22 |
| 4,838,853 | 6/1989 | Parisi | 606/169 |

(List continued on next page.)

FOREIGN PATENT DOCUMENTS

| | | | |
|---|---|---|---|
| 0 189 329 | 7/1986 | European Pat. Off. | A61B 17/22 |
| 0 615 907 | 9/1994 | European Pat. Off. | B65B 51/22 |
| 3-063041 | 3/1991 | Japan | A61B 17/22 |
| WO 90/01300 | 2/1990 | WIPO | A61B 17/32 |
| WO 91/19529 | 12/1991 | WIPO | A61M 29/02 |
| WO 94/05361 | 3/1994 | WIPO | A61M 25/00 |
| WO 95/22284 | 8/1995 | WIPO | A61B 08/12 |
| WO 95/24159 | 9/1995 | WIPO | A61B 17/36 |

OTHER PUBLICATIONS

Rosenschein, U. et al. "Experimental Ultrasonic Angioplasty: disruption of Atherosclerotic Plaques and Thrombi in Vitro and Arterial Recanalizaton in Vivo," (1990) JACC vol. 15, No. 3, pp. 711–717.

Yumita, N. et al. "Synergistic Effect of Ultrasound and Hematoporphyrin on Sarcoma 180," (1990) Jpn. J. Cancer Res. 81, pp. 304–308.

Tachibana, K. "Enhancement of Fibrinolysis with Ultrasound Energy," (1992) J. Vascular & Interventional Radiography 3 (2) pp. 299–303.

*Primary Examiner*—Michael Powell Buiz
*Assistant Examiner*—N. Kent Gring
*Attorney, Agent, or Firm*—Townsend and Townsend and Crew LLP

[57] ABSTRACT

An energy-transmitting catheter comprises a catheter body having a vibrating assembly at its distal end. The vibrating assembly comprises a magnetostrictive driver which is mechanically coupled to an interface member on the catheter for radiating energy into an environment surrounding the distal end of the catheter. Usually, the vibrating assembly further includes a tail mass, an interface member, and a spring element which together and in combination with the magnetostrictive driver define a resonant assembly for amplification of the displacement of the interface surface provided by the magnetostrictive driver. The catheter is useful for treating luminal conditions, such as vascular clot and plaque. Optionally, a therapeutic agent may be delivered through the catheter before, after, or simultaneously with the application of vibratory energy.

44 Claims, 4 Drawing Sheets

U.S. PATENT DOCUMENTS

| | | | |
|---|---|---|---|
| 4,870,953 | 10/1989 | DonMichael et al. | 128/24 |
| 4,936,281 | 6/1990 | Stasz | 128/660.03 |
| 4,948,587 | 8/1990 | Kost et al. | 424/435 |
| 4,978,333 | 12/1990 | Broadwin et al. | 604/22 |
| 5,085,662 | 2/1992 | Willard | 606/159 |
| 5,163,421 | 11/1992 | Berstein et al. | 128/24.1 |
| 5,197,946 | 3/1993 | Tachibana | 604/22 |
| 5,267,954 | 12/1993 | Nita | 904/22 |
| 5,267,985 | 12/1993 | Shimada et al. | 604/290 |
| 5,269,291 | 12/1993 | Carter | 128/24 |
| 5,269,297 | 12/1993 | Weng et al. | 128/24 |
| 5,279,546 | 1/1994 | Mische et al. | 604/225 |
| 5,282,785 | 2/1994 | Shapland et al. | 604/21 |
| 5,286,254 | 2/1994 | Shapland et al. | 604/21 |
| 5,304,115 | 4/1994 | Pflueger et al. | 604/22 |
| 5,315,998 | 5/1994 | Tachibana et al. | 128/660 |
| 5,318,014 | 6/1994 | Carter | 601/2 |
| 5,324,255 | 6/1994 | Passafaro et al. | 604/22 |
| 5,342,292 | 8/1994 | Nita | 604/22 |
| 5,344,395 | 9/1994 | Whalen et al. | 604/22 |
| 5,362,309 | 11/1994 | Carter | 604/22 |
| 5,371,520 | 12/1994 | Kubota | 347/11 |
| 5,380,273 | 1/1995 | Dubrul et al. | 604/22 |
| 5,397,301 | 3/1995 | Pflueger et al. | 604/22 |
| 5,447,509 | 9/1995 | Mills et al. | 606/1 |
| 5,456,259 | 10/1995 | Barlow et al. | 128/662.03 |
| 5,458,568 | 10/1995 | Racchini et al. | 604/19 |
| 5,458,631 | 10/1995 | Xavier | 607/117 |
| 5,462,523 | 10/1995 | Samson et al. | 604/30 |
| 5,465,725 | 11/1995 | Seyed-Bolorforosh | 128/662.03 |
| 5,474,530 | 12/1995 | Passafaro et al. | 604/22 |
| 5,474,531 | 12/1995 | Carter | 604/22 |

APPARATUS AND METHODS FOR VIBRATORY INTRALUMINAL THERAPY EMPLOYING MAGNETOSTRICTIVE TRANSDUCERS

BACKGROUND OF THE INVENTION

The present invention relates generally to medical devices and methods. More particularly, the present invention relates to apparatus and methods for the localized delivery of therapeutic vibratory energy within the vasculature and other body lumens.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

Bypass surgery can redirect blood around the obstructed artery resulting in improved blood flow. However, the resulting bypass grafts can themselves develop scar tissue and new blood clots in five to ten years resulting in blockage and the need for further treatment. In summary, all current therapies have limited long term success.

The use of ultrasonic energy has been proposed both to mechanically disrupt clot and to enhance the intravascular delivery of drugs to dissolve clot and inhibit restenosis. Ultrasonic energy may be delivered intravascularly using specialized catheters having an ultrasonically vibrating surface at or near their distal ends. One type of ultrasonic catheter employs a wire or other axial transmission element to deliver energy from an ultrasonic energy vibration source located outside the patient, through the catheter, and to the ultrasonically vibrating surface. While such systems can deliver relatively large amounts of energy, the need to transmit that energy through the entire length of the catheter presents a substantial risk to the patient.

Moreover, such catheters are typically rigid and cannot easily traverse narrow, tortuous arteries, such as the coronary arteries which frequently need to be treated. Because of their rigidity and inability to follow the vascular lumen, these catheters present a serious risk of vascular wall perforation.

In order to avoid the use of ultrasonic transmission members, catheters having ultrasonic transducers mounted directly on their distal ends have also been proposed. See, for example, U.S. Pat. Nos. 5,362,309; 5,318,014; 5,315, 998; 5,269,291; and 5,197,946. By providing the transducer within the catheter itself, there is no need to employ a transmission element along the entire length of the catheter. While such catheter designs offer enhanced safety, they suffer from a limited ability to generate large amounts of ultrasonic energy. Even though certain of these designs, such as that described in U.S. Pat. No. 5,362,309, employ "amplifiers" which enhance the delivery of ultrasonic energy, such designs are still problematic. In particular, the catheters of the '309 patent have relatively long, rigid transducers and are not amenable to receiving guidewires, both of which features make it difficult to position the catheters within the vasculature, particularly the coronary vasculature.

For these reasons, it would be desirable to provide improved energy-transmitting catheter designs which overcome at least some of the problems discussed above. In particular, it would be desirable to provide catheters having vibratory energy transducers at their distal ends, where the transducers are capable of oscillating interface surfaces with relatively high energy and amplitude. Additionally, it would be desirable to provide vibratory drivers which are capable of driving interface surfaces directly or in combination with resonant assemblies which amplify the displacement of the interface surface. It would further be desirable to provide transducer and driver designs which are highly efficient in order to minimize the production of heat within the vascular or other luminal environment. It would be still further desirable to provide methods for the intraluminal delivery of ultrasonic energy, where the ultrasonic energy is useful for a variety of purposes, including the direct mechanical disruption of clot, the enhancement of thrombolytic activity of agents to dissolve clot, and the enhancement of pharmacologic activity of agents to prevent restenosis of vascular sites previously treated by angioplasty or other interventional methods.

DESCRIPTION OF THE BACKGROUND ART

Catheters having ultrasonic elements with the capability of delivering thrombolytic and other liquid agents are described in U.S. Pat. Nos. 5,362,309; 5,318,014; 5,315, 998; 5,197,946; 5,397,301; 5,380,273; 5,344,395; 5,342, 292; 5,324,255; 5,304,115; 5,279,546; 5,269,297; 5,267, 954; 4,870,953; 4,808,153; 4,692,139; and 3,565,062; in WO 90/01300; and in Tachibana (1992) JVIR 3:299–303. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163, 421 and Rosenschein et al. (1990) JACC 15:711–717. Ultrasonically assisted atherectomy catheters are described in U.S. Pat. No. 5,085,662 and EP 189329. Ultrasonic enhancement of systemic and localized drug delivery is described in U.S. Pat. Nos. 5,286,254; 5,282,785; 5,267,985; and 4,948, 587; in WO 94/05361 and WO 91/19529; in JP 3-63041; and Yumita et al. (1990) JPN. J. CANCER RES. 81:304–308. An electrosurgical angioplasty catheter having ultrasonic enhancement is described in U.S. Pat. No. 4,936,281. An infusion and drainage catheter having an ultrasonic cleaning mechanism is described in U.S. Pat. No. 4,698,058. A drug delivery catheter having a pair of spaced-apart balloons to produce an isolated region around arterial plaque is described in U.S. Pat. No. 4,636,195.

Magnetostrictive transducers are described in U.S. Pat. Nos. 5,371,520 and 4,184,092, and EP 615 907.

SUMMARY OF THE INVENTION

According to the present invention, an energy-transmitting catheter comprises a catheter body having a proximal end and a distal end. A magnetostrictive driver is disposed near the distal end of the catheter body, and an interface surface is mechanically coupled to the driver so that the surface can be oscillated relative to the catheter body in order to radiate vibratory energy into a fluid environment surrounding the catheter. The magnetostrictive driver typically comprises a linear element composed of a magnetostrictive material, such as a polycrystalline alloy of terbium, dysprosium, and iron, and a coil disposed coaxially about the linear element. The coil is disposed to provide a magnetic field parallel to the longitudinal direction of the linear element. With increasing magnetic field strength, more magnetic domains change their alignment from random to parallel to the magnetic field, increasing the length of the linear element in direct proportion to the magnetic field strength. This realignment continues until all domains are parallel to the magnetic field, in which case, saturation has occurred. By driving the coil with an alternating current, a periodically reversing magnetic field will be induced in the linear element, causing the linear element to longitudinally oscillate at a frequency twice the frequency of the driving current. Alternatively, the linear element could be driven by combination of permanent magnets and an alternating field, or an alternating field with an offset, to produce magnetic fields of varying amplitude in one direction only. In this case, the magnetic domains are aligned parallel to the field only once during a cycle, producing longitudinal oscillations at the same frequency as that of the .driving current.

In the exemplary embodiment, the linear element of the magnetostrictive driver is a tube or a solid rod having a length in the range from 3 mm to 12 mm and a diameter in the range from 0.5 mm to 3 mm. The linear element will have a particular geometry and composition which permits oscillation at a desired drive frequency, determined by the frequency of the drive current, as just set forth. Preferably, the magnetostrictive driver will be included in a spring-mass assembly which further comprises a tail mass at or near the distal end of the catheter body and a spring element attaching the interface surface to the tail mass. By employing a relatively large tail mass, the resonant frequency of the interface member and spring element is independent of the tail mass and defined primarily by the mass of the interface member and the elastic modulus of the spring and magnetostrictive elements. By properly choosing the operating frequency of the longitudinally oscillating driver, the resonant system defined by the interface member, the spring element, and the magnetostrictive element can be resonantly driven to enhance both the displacement amplitude of an interface surface on the interface member and increase the efficiency of operation. i.e., the conversion of electrical energy to mechanical energy.

The spring element preferably comprises an axial member capable of mechanically coupling the interface member to the tail mass with sufficient space therebetween to receive the magnetostrictive driver. Typically, the spring element will comprise at least one rod secured at a proximal end to the tail mass and at a distal end to the interface member. The rod may optionally be tubular to provide the path for a guidewire, infusion of therapeutic agent, or the like. A single rod or tube will usually be disposed coaxially within the catheter. Multiple rods or tubes may be disposed symmetrically about the axis of the catheter body. Alternatively, the spring element may comprise a thin-walled cylindrical member secured to the tail mass and the interface member and enclosing the magnetostrictive driver in a concentric manner.

The interface member will usually include at least a distally disposed interface surface which forwardly transmits longitudinal oscillations into the environment surrounding the distal end of the catheter. Such a forwardly disposed interface surface will typically be convex, although it could be flat, concave, or irregular. Additionally, at least a portion of the interface surface may extend laterally over an axial surface of the member.

A method according to the present invention for treating intraluminal lesions or other target sites comprises providing a catheter having a magnetostrictive driver mechanically coupled to an interface surface at its distal end. A distal end of the catheter is advanced to a region near the target site, typically to a region of vascular stenosis within a patient's vasculature, and the interface surface is oscillated by the magnetostrictive driver. In this way, vibratory energy is efficiently delivered into the regions surrounding the distal end of the catheter. The interface surface is typically driven at a frequency in the range from 10 kHz to 300 kHz, and will have a longitudinal amplitude in the range from about 0.05 µm to 20 µm. The forwardly disposed surface of the interface member will typically have an area in the range from 0.5 $mm^2$ to 20 $mm^2$, and the catheter may be used in a variety of specific therapeutic protocols.

In a first such protocol, the interface member will be engaged directly against a vascular obstruction and used to ablate the structure by mechanical vibration and shearing or optionally to dissolve the structure with the simultaneous delivery of a thrombolytic or fibrinolytic agent. Alternatively, the catheter can be used to deliver vibratory energy into an environment where a thrombolytic or fibrinolytic agent has been delivered, where the catheter need not be directly engaged against clot or other stenoses. In such cases, the vibratory energy will enhance the activity of the therapeutic agent, typically by improving penetration of the agent into the clot. In a third exemplary protocol, the catheter may be used to deliver an anti-thrombotic agent to a previously treated vascular site to inhibit restenosis. Again, the vibratory energy will typically provide for enhanced delivery and penetration of the anti-thrombotic agent into the blood vessel wall.

DESCRIPTION OF THE SPECIFIC EMBODIMENTS

Figure 1:
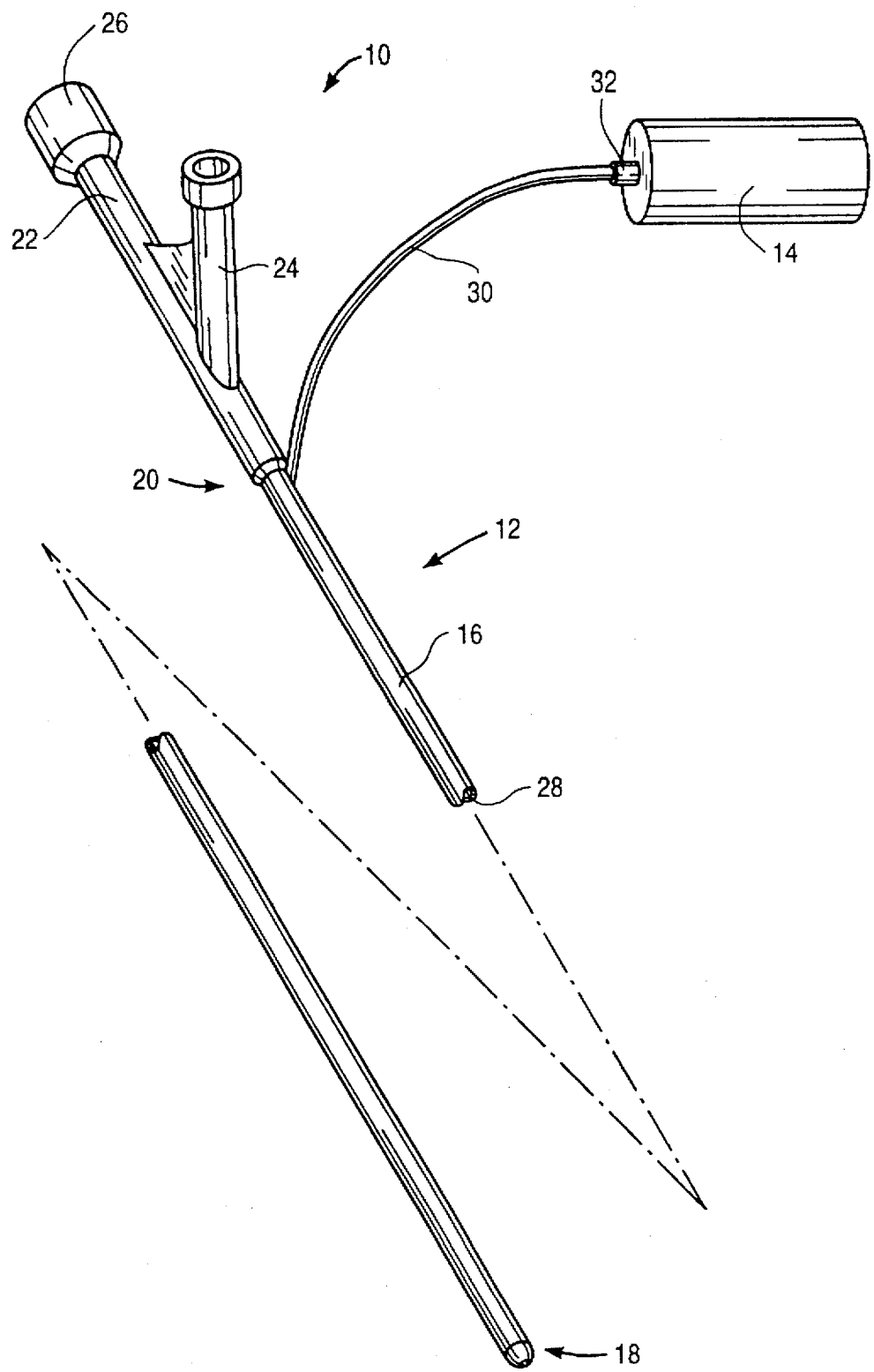
FIG. 1 illustrates an exemplary catheter incorporating a magnetostrictive driver constructed in accordance with the principles of the present invention.

The present invention provides apparatus and methods for the treatment of luminal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease. For example, catheters constructed according to the principles of the present invention can be used to directly engage and transmit vibratory, usually ultrasonic, energy into the stenotic material in order to mechanically disrupt the material to open the associated blood vessel lumen. Such mechanical disruption can be accomplished with or without the simultaneous administration of pharmacologic and therapeutic agents. The apparatus and methods of the present invention are also useful to enhance the administration of therapeutic agents, where the therapeutic agents are primarily responsible for the disruption of the stenotic material. In such cases, the catheter may be engaged against the stenotic material, or alternatively may be maintained a short distance away from the stenotic material. The vibratory energy will be relied on to agitate and promote the penetration of the therapeutic agent into the stenotic material. Suitable therapeutic agents include known thrombolytic and fibrinolytic drugs, such as heparin, tissue plasminogen activator (tPA), urokinase, streptokinase, and the like. The catheters and methods of the present invention are still further useful for the treatment of vascular sites which have been previously treated by other interventional techniques, such as angioplasty, atherectomy, laser ablation, and the like. In such cases, the catheters will be used to agitate and promote the penetration of anti-thrombogenic agents into the vascular or other luminal wall to inhibit restenosis. Suitable anti-thrombogenic agents include hirudin, hirulog, heparin, tPA, urokinase, streptokinase, and the like. In addition to treatment of the vascular system, the present invention may also be used for systemic and localized delivery of drugs within other body lumens, such as the ureter, the urethra, fallopian tubes, and the like. The present invention may further be used for the systemic and localized delivery of drugs within the vascular system for treatment of non-vascular diseases, e.g., for the treatment of tumors by the localized delivery of drugs to the vasculature supporting the tumor.

The catheter of the present invention will comprise a catheter body having a proximal end and distal end. The catheter body will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body may vary over its length, and different portions of the length may be formed from different materials. In the exemplary embodiment, the catheter body will comprise a single extrusion having at least one lumen therethrough. The lumen will usually be capable of receiving a guidewire, and may also be capable of delivering therapeutic agents and/or carrying electrical wires for connection from the proximal end of the catheter body to the distal end. Alternatively, the catheter body may include separate lumens for delivering therapeutic agent(s), routing electrical wires for connection to the ultrasonic transducer, or other purposes. The catheter body may be reinforced over all or a portion of its length. Conventional reinforcement materials include wire braids, wire meshes, wire coils, and the like. When employed with a guidewire for placement within the vasculature, the catheter body may have an "over-the-wire" design or a "rapid exchange" design. In the former case, the guidewire lumen will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less. Usually, a proximal housing will be secured to the proximal end of the catheter body, where the housing includes a guidewire port, a therapeutic agent infusion port, an electrical connector, and the like.

A longitudinally vibrating assembly is secured at or near the distal end of the catheter body. The assembly will include at least one interface surface, usually present on an interface member, which is vibrated at a desired frequency, wherein the interface surface is oriented to transmit vibrations to the fluid environment surrounding the distal end of the catheter. The vibrating assembly will usually be attached directly to the distal end of the catheter body but also could be disposed partially or totally within the distal end of the catheter body. Usually, the vibrating assembly will have a relatively short length, typically being below 2 cm, preferably being below 1 cm, and typically being in the range from about 0.4 cm to 1.5 cm, more usually in the range from about 0.6 cm to 1 cm. The assembly will preferably have a low profile (narrow diameter) to facilitate vascular or other intraluminal introductions, typically having a diameter below 6 mm, usually in the range from 1 mm to 5 mm, more usually in the range from 2 mm to 4 mm.

In the exemplary embodiment of the present invention, the interface surface will be forwardly disposed so that the surface may engage intraluminal obstructions as the catheter is advanced through the body lumen, such as a blood vessel. Such forwardly disposed vibrating surfaces will also be useful for projecting ultrasonic energy forwardly to agitate and promote absorption of a liquid therapeutic agent, which agent is usually delivered by the same catheter. In alternative embodiments, which are described in detail in copending application Ser. No. 08/566,739 pending, the interface surfaces may be laterally disposed to radiate ultrasonic energy radially outward from the catheter body.

The vibrating assembly of the present invention will usually be incorporated in a resonant spring-mass assembly which further comprises a tail mass and a spring element connecting the interface member to the tail mass. A magnetostrictive driver (as described more fully below) is disposed between the tail mass and the interface member. The mass of the tail mass will be substantially greater than that of the interface member, typically being at least four-fold greater, and usually being at least eight-fold greater. Usually, the mass of the tail mass will be in the range from about 0.1 gm to 10 gm, more usually in the range from about 0.2 gm to 4 gm. The mass of the interface member will be in the range from 0.01 gm to 1 gm, more usually in the range from 0.03 gm to 0.1 gm. In this way, the tail mass will remain substantially stationary or immobilized while the longitudinally oscillating driver imparts longitudinal (axial) movement to the interface member. The mass of the interface member and the elastic modulus of the spring element will be selected so that, when combined with the elastic modulus and other characteristics of the longitudinally oscillating driver, the resonantly vibrating assembly will resonate at a particular ultrasonic frequency, typically in the range from 10 kHz to 300 kHz, preferably from 20 kHz to 80 kHz. In this way, the longitudinally oscillating driver (when electronically driven) will drive the resonantly vibrating assembly at its resonant frequency, thus enhancing the efficiency of energy transfer and increasing the amplitude of vibration (displacement) of the interface member. Preferably, the interface member will operate with a displacement (under loaded conditions) of at least about 0.5 μm, preferably in the range from 0.05 μm to 20 μm, and more preferably in the range from 0.5 μm to 2 μm.

The tail mass will usually be formed separately from the catheter body and other components of the vibratory assembly, but optionally could be formed as part of the catheter body or alternatively as an integral unit with the spring element and/or interface member. The dimensions and shape of the tail mass will usually be selected to conform to the dimensions of the catheter body, i.e., usually being a short cylinder having a diameter which is the same as or slightly smaller than that of the distal end of the catheter body.

The interface member will usually form the distal-most tip of the catheter, and will usually have a forwardly disposed convex surface which defines the interface surface. The interface surface, however, need not be convex, and could alternatively be concave, flat, irregular, or have any other geometry capable of radiating ultrasonic energy forwardly as the interface member is vibrated. Typically, the interface surface will have an area in the range from 0.5 mm$^2$ to 20 mm$^2$, preferably from 3 mm$^2$ to 12 mm$^2$.

The spring element may comprise a single rod or tube extending distally from the tail mass and attached to the proximal surface of the interface member. Usually, a the single spring element will be disposed coaxially within the catheter. Alternatively, the spring element may comprise multiple rods or shafts, in which case they will usually be disposed symmetrically about the axis of the catheter.

One or more axial passages may be formed through the resonantly vibrating assembly, typically for passage of a guidewire, delivery of therapeutic agents, or the like. To provide such lumens, it will be necessary to form holes through both the tail mass and the interface member. Such holes can be aligned and joined by one or more axial components of the spring element, typically in the form of hollow tubes to provide a continuous lumen through the assembly. Alternatively, axial passages may be formed directly through the longitudinally oscillating driver.

The present invention will employ a magnetostrictive driver for oscillating the interface surface of the catheter. The magnetostrictive driver will generally be oriented to vibrate the interface surface on an interface member in the longitudinal or axial direction relative to the catheter body. The interface surface itself may be disposed on the interface member in a variety of orientations, but will usually be disposed laterally over a distal end of the catheter in order to transmit longitudinal oscillations into a fluid environment surrounding the distal end of the catheter. Alternatively, or additionally at least a portion of the interface surface may be disposed axially over a lateral surface of the catheter body in order to impart transverse vibrations in a radial direction from the catheter body. (See wave lines 93 in FIG. 7).

The fabrication of magnetostrictors for use as the magnetostrictive drivers in the catheters of the present invention is described generally in references, such as "Magnetostriction: Theory and Applications of Magnetoeleasticity," Etienne du Tremolet de Lacheisserie, CRC Press, 1993. Generally, the magnetostrictive drivers of the present invention will include at least one linear element having an axis parallel to, and usually coaxial with, the central axis of the catheter body. The linear element will be composed of a "magnetostrictive" material, i.e., a material which oscillates in a direction parallel to an applied magnetic field. The most common material presently available is a polycrystalline alloy of terbium, dysprosium, and iron ($Tb_{0.27} Dy_{0.73} Fe_2$). Such materials are advantageous as they provide a very high displacement, often over 0.1% of the total length of the linear element in the direction of oscillation, and sometimes over 0.2% of the total length, or higher. Magnetostrictors are driven by applying a magnetic field parallel to the expansion axis of the linear element. For optimum performance, the magnetic field must be uniform over the entire length of the linear element, and magnetic field intensities in the range from 200 to 1200 Oerstads will typically be employed. The higher the intensity of the magnetic field, the greater the expansion, with expansions in the range from 0.1% to 0.2% presently being attainable. For increased displacement, the linear element of the magnetostrictor may also be placed under compressive forces in a direction parallel to the expansion axis of the material. Typical compressive forces will be in the range from 1 to 4 kPSI, preferably from 1.5 to 2.5 kPSI.

The magnetostrictor expands and contracts in length as a result of the application and cessation of a magnetic field parallel to the direction of expansion. The expansion results from the alignment of magnetic domains within the material when the magnetic field is present. If the field is reversed, the magnetic domains reverse, again causing expansion of the material. It will thus be appreciated by applying an alternating or reversing magnetic field, the linear element of the magnetostrictor of the present invention will expand and contract at a frequency twice that of the frequency of the field. Alternatively, by biasing a magnetic field to provide only positive (or negative) components, the linear element could be driven at a frequency equal to that of the frequency of the field. The biased magnetic field may be achieved by either the combination of permanent magnetic and an alternating magnetic field of by the electrical bias to the alternating current driving the magnetic field coils.

In preferred embodiments of the present invention, the linear element of the magnetostrictor will be driven by an electrically conductive coil disposed about the linear element. An alternating magnetic field can then be induced by applying an alternating current to the coil in a conventional manner. The magnetic strength will be directly dependent on the design of the magnetic coil surrounding the magnetorestricive element. A coil of 80 turns with a length of one centimeter and a current of two amps will have a field strength of typically 200 Oerstads. Typically, the peak applied current will be in the range from 0.5 to 10 A, preferably from 1 to 3 A. The coil will preferably extend beyond the proximal and distal ends of the linear element of the driver in order to assure uniformity of the applied magnetic field. Additionally, it is important that all materials of construction used in the distal end of the catheter be non-magnetic. In particular, for the metal components, as described below, it is preferable to use a non-magnetic stainless steel in order to avoid perturbing the uniformity of the applied magnetic field.

As mentioned above, it is necessary that the magnetostrictive linear element be axially compressed in order to achieve maximum displacement. Such axial compression will usually be achieved by a linear spring element having flanges or other members for engaging the proximal and distal ends of the linear driving element and applying a constant axial compression. In the preferred elements, the spring element and flanges or other constraining means will be provided by a resonant assembly including a tail mass and the interface member, which are disposed on the proximal and distal sides of the linear driving element, respectively. Such assemblies are described in greater detail below.

The dimensions of the linear element of the magnetostrictor will be chosen to be compatible with the dimensions of the catheter. Typically, the linear element will have a length in the range from 3 mm to 12 mm, preferably from 4 mm to 6 mm. For coaxial linear elements, the diameter will typically be in the range from 0.5 mm to 3 mm, preferably from 1 mm to 2 mm. Frequently, the linear element will be in the form of a tube having the outer dimensions set forth above and an inner lumen having a diameter in the range from 1 mm to 1.5 mm. The lumen will provide for placement of the spring element, an infusion path for therapeutic and pharmacologic agents, and/or a guidewire lumen.

The spring element which joins the interface member to the tail mass may comprise a single component, e.g., a single solid rod or hollow tube disposed along the longitudinal axis of the catheter or a cylindrical shell either within or external to the longitudinally oscillating driver. Alternatively, the spring element may comprise a plurality of components, such as a plurality of rods or tubes disposed symmetrically about the longitudinal axis of the catheter. The spring element may be composed of any of a wide variety of materials, most typically being a non-magnetic stainless steel, such as a hardened stainless steel having a Rockwell stiffness of at least about 35. The cross-sectional area of the spring element(s) shall be sufficient to provide a maximum tension of approximately 20% of the tensile strength of the material, typically about 25,000 PSI, at the time when the spring experiences its maximum deformation, i.e., the time of maximum forward displacement of the interface member. The assembly of the tail mass, interface member, and longitudinally oscillating driver is compressed by the spring mass with a static force sufficient to present continuing compressive forces at the time when the assembly shrinks to its minimum longitudinal displacement. The interface member and spring mass shall have a mass and stiffness which together assure that the spring element retains compressive force on the interface member at the time of maximum reverse acceleration in order to prevent the interface mass from separating from the driving element. The time of maximum reverse acceleration occurs at the time of maximum forward displacement.

Referring now to FIG. 1, a catheter system 10 comprising a catheter 12 constructed in accordance with the principles of the present invention and a power supply 14 is illustrated. The catheter 12 includes a catheter body 16 having a distal end 18 and a proximal end 20, a proximal housing 22 having a fluid infusion port 24, and a guidewire port 26. The catheter 12 includes at least a single lumen 28 extending from the proximal end 20 to the distal end 18 and connected to both the fluid infusion port 24 and the guidewire port 26. Usually, the catheter 12 will have at least a second lumen (not illustrated) for accommodating wires (separate from the guidewire/fluid infusion lumen). A cable 30 extends from the proximal end 20 of the catheter body 16 (typically through the lumen 28) and includes a connector 32 which may be removably attached to the power supply 14. The power supply 14 will be selected to drive the magnetostrictive driver at a about preselected frequency. The power supply 14 will be selected to provide an alternating current source for connection to the magnetostrictive driver. As with conventional ultrasonic transducers, the drive frequency of the linear element of the magnetostrictive driver will depend principally on the resonant structure of the driver which is determined by the mass of the interface member and the elastic modulus of the spring element and of the drive element. Thus, the power supply 14 will be selected to operate at a frequency or frequencies consistent with the resonant frequency of the catheter itself. The operational range is typically from 10 kHz to 300 kHz, preferably from 20 kHz to 80 kHz. For example, the power supply 14 may comprise a conventional signal generator, such as those commercially available from suppliers such as Hewlett-Packard, Palo Alto, Calif., and Tektronics, Portland, Oreg., and a power amplifier, such as those commercially available from suppliers such as ENI, Rochester, N.Y., and Krohn-Hite Corporation, Avon, Mass.. Alternatively, the power supply might comprise custom signal generator and power amplifier circuits with tracking circuits to maintain the driving frequency at the catheter resonant frequency as the resonant frequency drifts due to thermally induced material variations.

Figure 2:
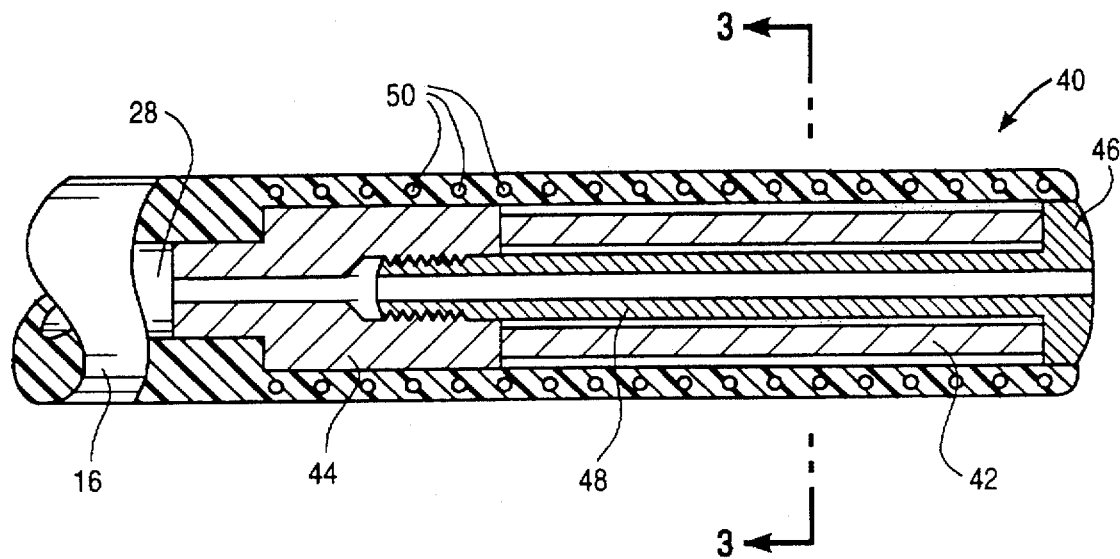
FIG. 2 is a detailed view of the distal end of the catheter of FIG. 1, shown in partial section.
Figure 3:
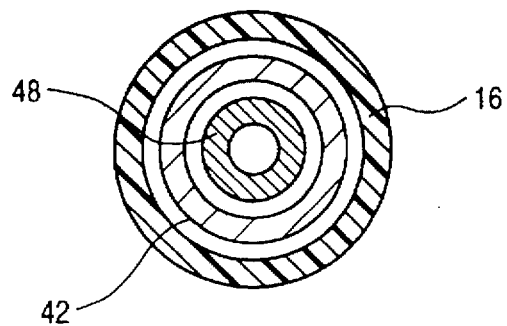
FIG. 3 is a cross-sectional view taken along line 3—3 of FIG. 2.

Referring now to FIGS. 2 and 3, a first specific embodiment of a magnetostrictive driver assembly constructed in accordance with the principles of the present invention will be described. The magnetostrictive driver assembly 40 includes a tubular, linear element 42, disposed between a tail mass 44 and an interface member 46. The tail mass 44 and interface member 46 are joined by a tubular spring element 48, where the interface member 46 is shown to be integrally formed with the spring element 48. Such integral construction is not a requirement of the present invention and the interface member 46 could be attached to a separate spring element in a variety of conventional manners, such as using threads, welding, or the like. Similarly, the proximal end at the spring element 48 is shown to be threadably attached to the tail mass. The attachment could be achieved by a variety of other techniques, again including welding, or the like. Generally, however, it will be desirable that at least one of the interface member 46 and the tail mass 44 be capable of linear adjustment relative to the spring element 48. Particularly, it will be necessary to provide a compressive force on the linear element 42, and it will be desirable to adjust the compressive force during catheter fabrication by adjusting the relative linear positions of the tail mass 44 and interface member 46 by some very small amount. It will further be desirable if the spring force of the spring element 48 and mass of the interface member 46 are selected to provide for resonant operation of the assembly 40, as generally described above.

The tail mass 44 will be secured directly to the proximal end of the catheter body 16, using adhesives, heat fusion, or other conventional techniques. A magnetic drive coil 50 will be disposed concentrically about the linear element 42, preferably overlapping the linear element 42 at both the proximal and distal ends. As illustrated, the coil 50 is embedded in the polymeric matrix of the catheter body 16. It would also be possible to provide the coil as a separate component apart from the catheter body.

Figure 4:
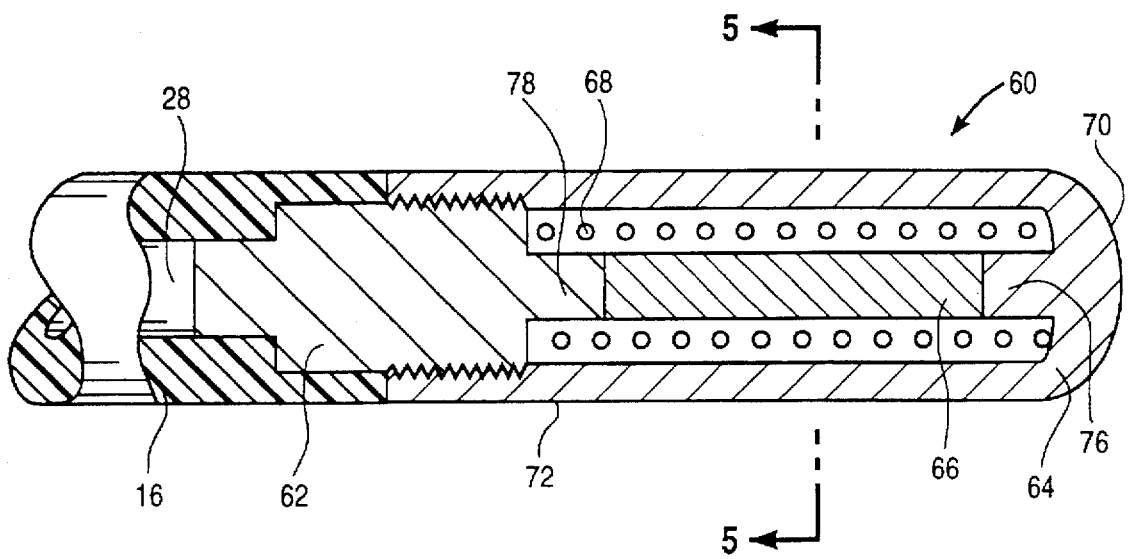
FIG. 4 is an alternative detailed view of the distal end of the catheter of FIG. 1, shown in partial section.
Figure 5:
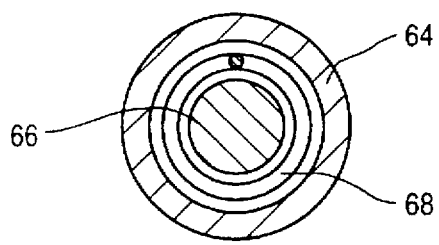
FIG. 5 is a cross-sectional view taken along line 5—5 of FIG. 4.

Referring now to FIGS. 4 and 5, an alternative embodiment of the magnetostrictive driver assembly of the present invention will be described. The assembly 60 comprises a tail mass 62, an interface member 64, a linear element 66, and a drive coil 68. The interface member 64 is configured to provide both a first region 70 which extends laterally over the distal end of the catheter and a second region 72 which extends axially over a lateral surface of the catheter body. The linear member 66 is disposed between a first abutment member 76 which is formed integrally with the interface member 64 and a second abutment member 78 which is formed as part of the tail mass 62. The abutment members help assure that the drive coil 68 extends substantially beyond both the proximal and distal ends of the linear element 66. Such extensions help assure the uniformity of the magnetic field which is applied. Although illustrated as a solid rod, the linear element 66 could be formed as a tube with a lumen suitable for receiving a guidewire, providing fluid delivery, and the like. In such cases, the tail mass 62 and interface member 64 would be provided with corresponding, coaxial lumens.

Figure 6:
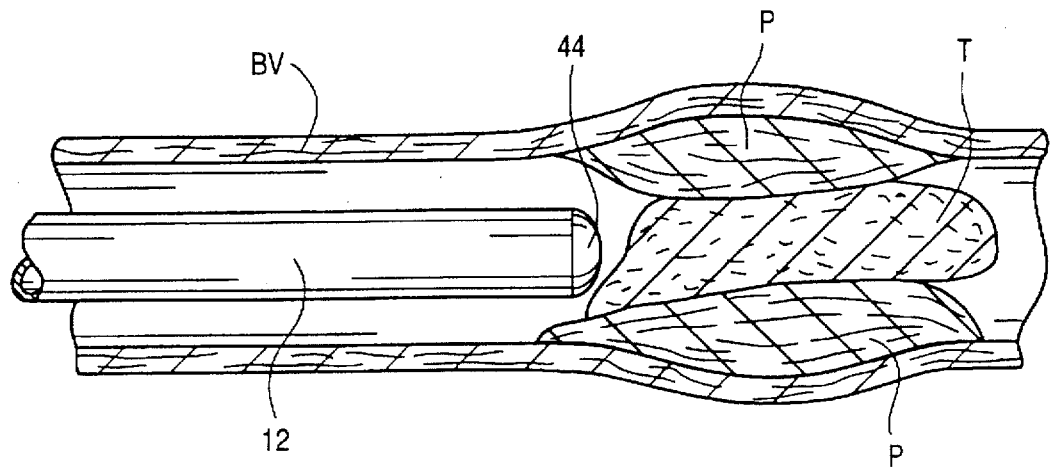
FIG. 6 illustrates the use of the catheter of FIG. 1 in a first protocol for ablating clot by direct engagement of an interface surface on the catheter of FIG. 1 with the clot.

Referring now to FIG. 6, use of the catheter 12 for directly engaging a region of thrombus T in a diseased blood vessel BV having a region of plaque is illustrated. The forwardly disposed interface surface of interface member 44 is advanced through the lumen of the blood vessel in a conventional manner until it engages the thrombus T. The resonantly vibrating assembly will then be activated (by applying an alternating current to drive coil 50) to cause longitudinal vibration of the interface member 44. The interface surface of the interface member, in turn, will transmit the vibrations directly into the thrombus T, resulting in mechanical disruption of the thrombus and clot. Optionally, a thrombolytic or fibrinolytic agent may be delivered through the catheter 12 and released into a region proximal to the thrombus T, either before, during or after the mechanical disruption. Preferably, the ultrasonic energy will be transmitted while the treatment agent is being released to enhance penetration of the agent into the thrombus T.

Figure 7:
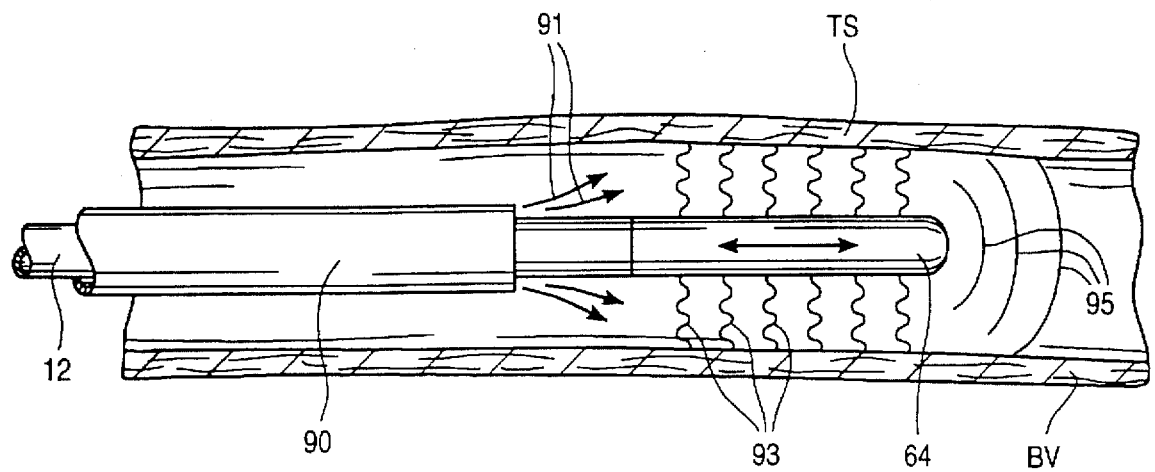
FIG. 7 illustrates the use of the catheter of FIG. 1 in a second protocol for enhancing the activity of the therapeutic agent released from the catheter by imparting vibratory energy into the environment surrounding the catheter using the interface surface.

An alternative treatment method employing the catheter 12 of FIGS. 4 and 5 is illustrated in FIG. 7. There, a sleeve catheter 90 is disposed over the catheter 12, and an anti-thrombogenic treatment agent is delivered to a target site TS within a blood vessel BV through an annular lumen defined between the sleeve and catheter 12, as indicated by arrows 91. The interface member 64 is oscillated, as described previously. The vibration will enhance penetration of the agent into the wall of the blood vessel BV. This method would be equally suitable for delivering drugs into other body lumens. Use of the sleeve catheter 90 for delivering drugs is illustrated as an alternative to delivering the drugs through the lumen of the catheter 12 itself. It will be appreciated that the sleeve catheter 90 could have been used in the method of FIG. 6. Conversely, the lumen of catheter 12 could have been used to deliver the anti-thrombogenic agent in the method of FIG. 7. The interface member 64 results in transverse waves 93 emanating radially from a lateral surface thereof as well as longitudinal waves 95 emanating forwardly from the distal end of the catheter. Such wave patterns are particularly advantageous for enhancing drug penetration into the luminal wall. Optionally, an annular air gap (not shown) could be left around the driver 66.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An energy-transmitting catheter, said catheter comprising:
    a flexible catheter body having a proximal end and a distal end;
    a magnetostrictive driver disposed near and within the distal end of the catheter body; and
    an interface surface mechanically coupled to the driver so that said surface can be oscillated relative to the catheter body.

2. An energy-transmitting catheter as in claim 1, wherein the magnetostrictive driver comprises a linear element and a coil disposed coaxially about the linear element.

3. An energy-transmitting driver as in claim 2, wherein the linear element has a geometry and is composed of a material which provide oscillation at a frequency in the range from 10 kHz to 300 kHz.

4. An energy-transmitting catheter as in claim 2, wherein the linear element is composed of a polycrystalline alloy of terbium, dysprosium, and iron.

5. An energy-transmitting catheter as in claim 2, wherein the linear element is a tube or a solid rod having a length in the range from 3 mm to 12 mm and a diameter in the range from 0.5 mm to 3 mm.

6. An energy-transmitting catheter as in claim 1, wherein the magnetostrictive driver is included in a resonant spring-mass assembly.

7. An energy-transmitting catheter as in claim 6, wherein the resonant spring-mass assembly comprises
    an interface member having the interface surface thereon;
    a tail mass at the distal end of the catheter body; and
    a spring element attached to and extending between the tail mass and the interface member with the magnetostrictive driver therebetween;
    wherein the tail mass has a mass which is much greater than that of the interface member and wherein the spring element provides a spring force in combination with the elastic modulus of the magnetostrictive driver which permits resonant driving by the magnetostrictive driver.

8. An energy-transmitting catheter as in claim 7, wherein the tail mass has a mass which is at least four times the mass of the interface member.

9. An energy-transmitting catheter as in claim 8, wherein the tail mass has a mass in the range from 0.1 gm to 10 gm and the interface member has a mass in the range from 0.01 gm to 1 gm.

10. An energy-transmitting catheter as in claim 7, wherein the spring element comprises at least one rod secured at a proximal end to the tail mass and at a distal end to the interface member.

11. An energy-transmitting catheter as in claim 10, wherein the spring element consists of a single rod disposed coaxially within the catheter.

12. An energy-transmitting catheter as in claim 10, wherein the spring element comprises at least two parallel rod members disposed symmetrically about the axis of the catheter body.

13. An energy-transmitting catheter as in claim 1, wherein the interface surface includes at least a portion which extends laterally over a distal end of the catheter and which forwardly transmits longitudinal oscillations into the environment surrounding the distal end of the catheter.

14. An energy-transmitting catheter as in claim 13, wherein the interface surface has a generally convex shape.

15. An energy-transmitting catheter as in claim 1, wherein the interface surface includes at least a portion which extends axially over a lateral surface of the catheter body.

16. An energy-transmitting catheter as in claim 1, wherein the catheter body has at least one lumen for delivering a therapeutic agent therethrough.

17. An improved ultrasonic catheter of the type comprising a flexible catheter body having a peripheral surface and an ultrasonic driver near a distal end thereof, wherein the improvement comprises a magnetostrictive driver mechanically coupled to an interface surface on the catheter body, wherein the magnetostrictive driver is disposed entirely within the peripheral surface of the catheter body.

18. An improved catheter as in claim 17, wherein the magnetostrictive driver comprises a linear element and a coil disposed coaxially about the linear element.

19. An improved driver as in claim 18, wherein the linear element has a geometry and is composed of a material which provides oscillation at a frequency in the range from 10 kHz to 300 kHz.

20. An improved catheter as in claim 18, wherein the linear element is composed of a polycrystalline alloy of terbium, dysprosium, and iron.

21. An improved catheter as in claim 18, wherein the linear element is a tube or a solid rod having a length in the range from 3 mm to 12 mm and a diameter in the range from 0.5 mm to 3 mm.

22. An energy-transmitting catheter as in claim 17, wherein the magnetostrictive driver is included in a resonant spring-mass assembly.

23. An energy-transmitting catheter as in claim 22, wherein the resonant spring-mass assembly comprises an interface member having the interface surface thereon;

a tail mass at the proximal end of the catheter body; and a spring element attached to and extending between the tail mass and the interface member with the magnetostrictive driver therebetween;

wherein the tail mass has a mass which is much greater than that of the interface surface and wherein the spring element provides a spring force which permits resonant driving by the magnetostrictive driver.

24. An improved catheter as in claim 23, wherein the tail mass has a mass which is at least four times the mass of the interface member.

25. An improved catheter as in claim 24, wherein the tail mass has a mass in the range from 0.1 gm to 10 gm and the interface member has a mass in the range from 0.01 gm to 1 gm.

26. An improved catheter as in claim 23, wherein the spring element comprises at least one rod secured at a proximal end to the tail mass and at a distal end to the interface member.

27. An improved catheter as in claim 26, wherein the spring element consists of a single rod disposed coaxially within the catheter.

28. An improved catheter as in claim 26, wherein the spring element comprises at least two parallel rod members disposed symmetrically about the axis of the catheter body.

29. An energy-transmitting catheter as in claim 17, wherein the interface surface includes at least a portion which extends laterally over a distal end of the catheter and which forwardly transmits longitudinal oscillations into the environment surrounding the distal end of the catheter.

30. An improved catheter as in claim 29, wherein the interface surface has a generally convex shape.

31. An improved catheter as in claim 17, wherein the interface member includes at least a portion which extends axially over a lateral surface of the catheter body.

32. An improved catheter as in claim 17, wherein the catheter body has at least one lumen for delivering a therapeutic agent therethrough.

33. A method for treating an intraluminal target site, said method comprising:

providing a flexible catheter having a magnetostrictive driver disposed at and within a distal end of the catheter, wherein the magnetostrictive driver is mechanically coupled to an interface surface near the distal end of the catheter;

advancing the distal end of the catheter to an intraluminal region near the target site; and energizing the magnetostrictive driver to oscillate the interface surface and impart vibratory energy into a fluid environment surrounding the distal end of the catheter.

34. A method as in claim 33, wherein the intraluminal target site contains a vascular stenosis.

35. A method as in claim 34, wherein the interface member surface is engaged against a vascular obstruction.

36. A method as in claim 33, wherein the interface surface is oscillated at a frequency in the range from about 10 kHz to 300 kHz.

37. A method as in claim 36, wherein the interface member is driven with a longitudinal amplitude in the range from 0.05 µm to 20 µm.

38. A method as in claim 33, wherein at least a portion of the interface surface extends laterally over the distal end of the catheter.

39. A method as in claim 38, wherein the laterally extending portion of the interface surface has an area in the range from 0.5 mm$^2$ to 20 mm$^2$.

40. A method as in claim 33, wherein at least a portion of the interface surface extends axially over a lateral surface of the catheter body.

41. A method as in claim 33, further comprising delivering a therapeutic agent through the catheter to the intraluminal lesion.

42. A method as in claim 41, wherein the therapeutic agent is delivered while ultrasonic energy is being radiated into the region.

43. A method as in claim 42, wherein the therapeutic agent is a fibrinolytic agent delivered to a vascular stenosis to treat clot.

44. A method as in claim 42, wherein the therapeutic agent is delivered to a previously treated vascular site to inhibit restenosis.

* * * * *